United States Patent
Klein et al.

(10) Patent No.: US 9,528,156 B2
(45) Date of Patent: Dec. 27, 2016

(54) METHOD FOR DETERMINING THE PREDISPOSITION OF A PATIENT TO CHANGED BIOTRANSFORMATION AND TO THE DEVELOPMENT OF UNDESIRED DRUG EFFECTS IN A TREATMENT OF THE PATIENT WITH ATROVASTATIN

(75) Inventors: Kathrin Klein, Stuttgart (DE); Stephan Riedmaier, Stuttgart (DE); Ulrich Zanger, Korntal (DE)

(73) Assignee: Robert Bosch GmbH, Stuttgart (DE)

(*) Notice: Subject to any disclaimer, the term of this patent is extended or adjusted under 35 U.S.C. 154(b) by 465 days.

(21) Appl. No.: 13/260,508

(22) PCT Filed: Feb. 23, 2010

(86) PCT No.: PCT/EP2010/052245
§ 371 (c)(1),
(2), (4) Date: Dec. 29, 2011

(87) PCT Pub. No.: WO2010/108737
PCT Pub. Date: Sep. 30, 2010

(65) Prior Publication Data
US 2012/0107814 A1    May 3, 2012

(30) Foreign Application Priority Data
Mar. 26, 2009    (DE) .................... 10 2009 015 978

(51) Int. Cl.
*C12Q 1/68*    (2006.01)

(52) U.S. Cl.
CPC ....... *C12Q 1/6883* (2013.01); *C12Q 2600/106* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 6,479,236 B2 | 11/2002 | Penny et al. | |
| 6,528,260 B1 | 3/2003 | Blumenfeld et al. | |
| 7,407,772 B2 * | 8/2008 | Prueksaritanont ... | A61K 31/366 435/15 |
| 2002/0061518 A1 | 5/2002 | Penny et al. | |

FOREIGN PATENT DOCUMENTS

WO    2008/032921 A1    3/2008

OTHER PUBLICATIONS

Iwai et al. J Hum Genet (2004) 49:123-128.*
Caillier et al. (Pharmacogenetics and Genomics 2007, 17:481-495).*
Riedmaier et al. (Clinical Pharmacology & Therapeutics, published online Sep. 30, 2009, vol. 87, No. 1, pp. 65-73).*
Andiappan (BMC Genetics. 2010. 11: 36).*
Sotos et al. Statistics Education Research Journal Nov. 2009, 8(2):33-55.*
Terwilliger and Hiekkalinna European Journal of Human Genetics (2006) 14, 426-437. doi:10.1038/sj.ejhg.5201583; published online Feb. 15, 2006.*
Langford et al. (Langford et al. (The American Statistician, Nov. 2001, vol. 55, No. 4)).*
Zill et al. Molecular Psychiatry (2004) 9, 1030-1036.*
Langdahl (Journal of Bone and Mineral Research 2000 vol. 15, No. 3, pp. 402-414).*
Wall (Nature Reviews Genetics (2003) vol. 4, pp. 587-597).*
Hegele Arterioscler Thromb Vasc Biol 2002;22;1058-1061.*
Lucentini (2004) The Scientist. p. 20.*
Chen et al. Drug Metabolism and Disposition, 2006, vol. 34, No. 9, pp. 1462-1467.*
Supplemental Table 2 from Riedmaier et al. (Clinical Pharmacology & Therapeutics, published online Sep. 30, 2009) two pages of supplemental table, obtained from www.nature.com/cpt.*
Fu et al. Leukemia (2008) 22, 660-663; doi:10.1038/sj.leu.2404931; published online Aug. 30, 2007.*
GenBank AY705979 Homo sapiens truncated UDP glycosyltransferase 1 family, polypeptide A3 (UGT1A3) gene, complete cds. 3 pages.*
Neil et al.(Int. J. Clin. Pract., Sep. 1999, vol. 53, No. 6, 422-426).*
Plosker et al. (Drugs 2000, vol. 60, No. 5, pp. 1179-206).*
Thompson et al. (The Pharmacogenomics Journal (2005) 5, 352-358).*
Usher-Smith et al. (Int J Clin Pract, Jan. 2007, 61, 1, 15-23).*
International Search Report corresponding to PCT Application No. PCT/EP2010/052245, mailed May 31, 2010 (German and English language document) (6 pages).
Russell A. Wilke et al., Relative Impact of CYP3A Genotype and Concomitant Medication on the Severity of Atorvastatin-Induced Muscle Damage, Pharmacogenetics and Genomics, Jun. 2005, vol. 15, No. 6, pp. 415-421, Lippincott Williams & Wilkins, XP008077717.
Yakun Chen et al., Genetic Variants of Human UGT1A3: Functional Characterization and Frequency Distribution in a Chinese Han Population, Drug Metabolism and Disposition, 2006, vol. 34 No. 9, pp. 1462-1467, The American Society for Pharmacology and Experimental Therapeutics, United States XP002582410.

(Continued)

*Primary Examiner* — Juliet Switzer
(74) *Attorney, Agent, or Firm* — Norton Rose Fulbright US LLP; Gerard Messina

(57) ABSTRACT

A method for determining a predisposition of a patient to the development of muscular diseases and/or to changed biotransformation in a treatment of the patient with atorvastatin is disclosed. The presence of at least one single nucleotide polymorphism (SNP) in the UGT1A3 gene (uridine diphosphate glucuronosyltransferase gene 1A3) and/or an increased UGT1A3 gene expression is determined in a biological sample of the patient. The disclosure further relates to oligonucleotides that can be used in the method and to diagnostic kits that use the oligonucleotides.

17 Claims, 7 Drawing Sheets

(56) References Cited

OTHER PUBLICATIONS

Ine Blankenberg Skottheim et al., Statin Induced Myotoxicity: The lactone forms are more potent than the acid forms in human skeletal muscle cells in vitro, European Journal of Pharmaceutical Sciences, Apr. 2008, vol. 33, No. 4-5, pp. 317-325, Elsevier, Amsterdam, NL, XP022586184.

S. Riedmaier et al., UDP-Glucuronosyltransferase (UGT) Polymorphisms Affect Atorvastatin Lactonization In Vitro and In Vivo, Clinical Pharmacology & Therapeutics, Jan. 2010, vol. 87, No. 1, pp. 65-73, XP002582411.

Hermann, et al., Exposure of Atorastatin is Unchanged but Lactone and Acid Metabolites are Increased Several-Fold in Patients with Atorvastatin-Induced Myopathy, Clinical Pharmacology and Therapeutics, Jun. 2006, pp. 532-539, 79-6, The American Society for Clinical Pharmacology and Therapeutics, Oslo, Norway.

Lankisch, et al., Aryl hydrocarbon receptor-mediated regulation of the human estrogen and bile acid UDP-glucuronosyltransferase 1A3 gene, Arch. Toxicol., 2008, vol. 82, pp. 573-582.

Prueksaritanont, et al., Glucuronidation of Statins in Animals and Humans: A Novel Mechanism of Statin Lactonization, Department of Drug Metabolism, Jan. 18, 2002, pp. 505-512, 30-5, The American Society for Pharmacology and Experimental Therapeutics, West Point, Pennsylvania.

Homo sapiens UDP glucuronosyltransferase 1 family, polypeptide A3 (UGT1A3), mRNA, NCBI Reference Sequence: NM_019093.2 (Dec. 21, 2008).

Jacobsen et al. Drug Metabolism and Disposition vol. 28, No. 11, 2000, pp. 1369-1378.

Goosen et al.: 'Atorvastatin glucoronidation is minimally and nonselectively inhibited by the Fibrates Gemfibrozil, Fenofibrate, and Fenofibric Acid' Drug Metaboism and Disposition. vol. 35, No. 8, 2007, pp. 1315-1324.

Menard V. et al.: 'Analysis of inherited genetic variations at the UGT1 locus in the French-Canadian population' Hum an Mutattion, vol. 30, Issue 4, Feb. 8, 2009.

Wolbold et al.: 'Sex is a Major Determinant of CYP3A4 Expression in Human Liver' Hepatology, Oct. 2003; 38 (4):978-88.

Lang et al.: 'Extensive genetic polymorphism in the human CYP2B6 gene with impact on expression and function in human liver' Pharmacogenetics vol. 11, 2001, pp. 399-415.

Lankisch et al.: 'Aryl hydrocarbon receptor-mediated regulation of the human estrogen and bile acid UDP-glucuronosyltransferase 1A3 gene' Arch Toxicol. Sep. 2008;82(9):573-582.

\* cited by examiner

Mutation

Exons

| genom. Position in AF297093 | rs number | Promoter + exon1 region | Base substitution | Reference sequence | UGT1A3*1 | UGT1A3*2a | UGT1A3*2b | UGT1A3*2c | UGT1A3*3a | UGT1A3*6a | UGT1A3*9a |
|---|---|---|---|---|---|---|---|---|---|---|---|
| 144977 | rs55772651 | -758 | A>G | A | G | G | G | G | G | G | G |
| 144884 | rs1983023 | -751 | T>C | T | C | C | C | C | C | C | C |
| 145154 | rs56304713 | -581 | C>T | C | T | T | T | T | T | | |
| 145182 | rs45507691 | -553 | G>A | G | | A | | A | | | |
| 145587 | rs3806597 | -204 | A>G | A | G | G | G | G | G | G | G |
| 145669 | rs3806596 | -66 | T>C | T | C | C | C | C | C | C | C |
| 145751 | rs28898617 | Q6R | A>G | A | | | | | | | |
| 145765 | rs3821242 | W11R | T>C | T | C | C | C | C | C | C | C |
| 145815 | rs6706232 | E27E | G>A | G | A | A | A | A | A | A | A |
| 145874 | rs6431625 | V47A | T>C | T | C | C | C | C | | C | C |
| 145968 | rs17868336 | T78T | A>G | A | | | | G | | | |
| 146062 | not available | F110I | T>A | T | | | | | | | |
| 146076 | rs28898619 | M114I | G>A | G | | | | | | | |
| 146207 | not available | A158V | C>T | C | | | | | | | |
| 146211 | rs7574296 | A159A | A>G | A | G | G | G | G | G | | G |
| 146253 | rs45586035 | frameshift | G> | G | | | | | | | |
| 146271 | not available | D179D | T>C | T | | | | | | | |
| 146356 | rs140767748 | M208L | A>C | A | | | | | | | C |
| 146542 | rs45449995 | M270V | A>G | A | | G | | | | | |

Fig. 4

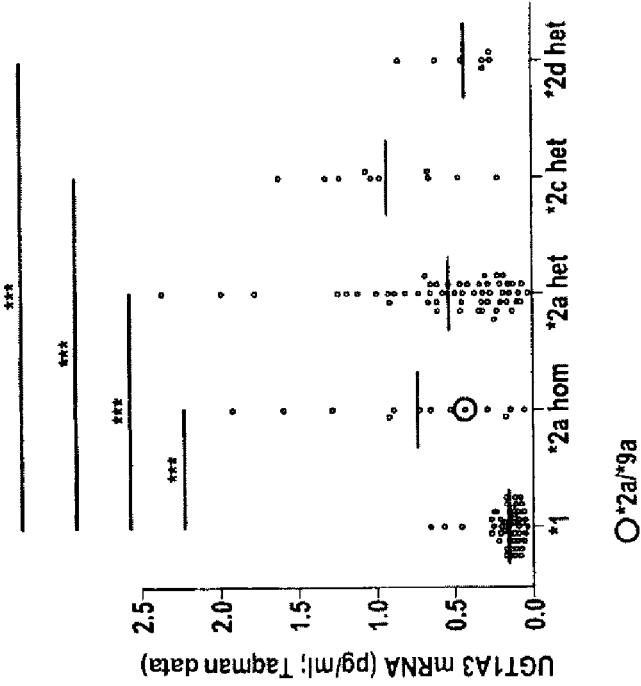
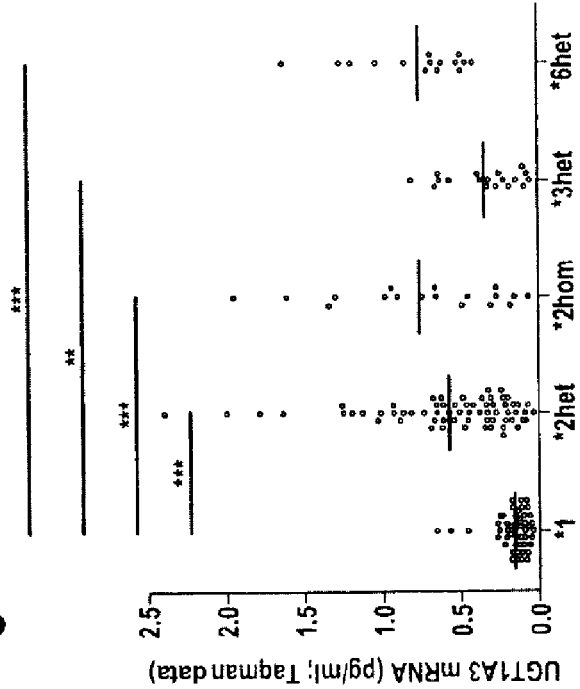

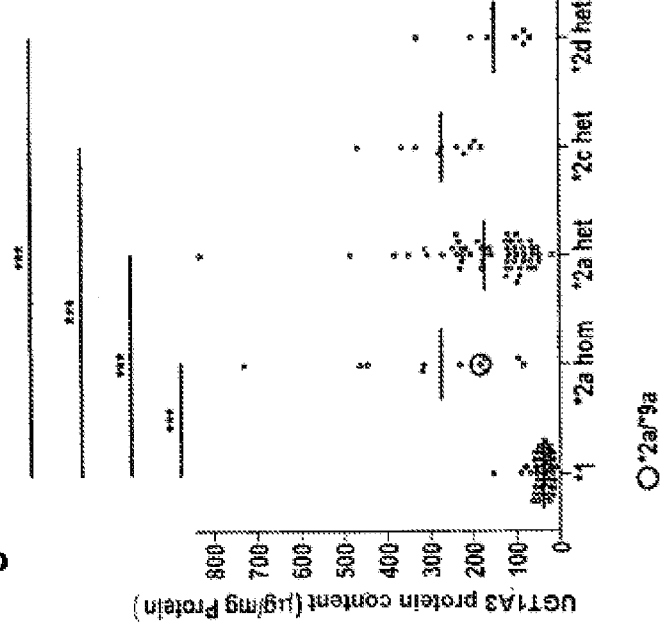
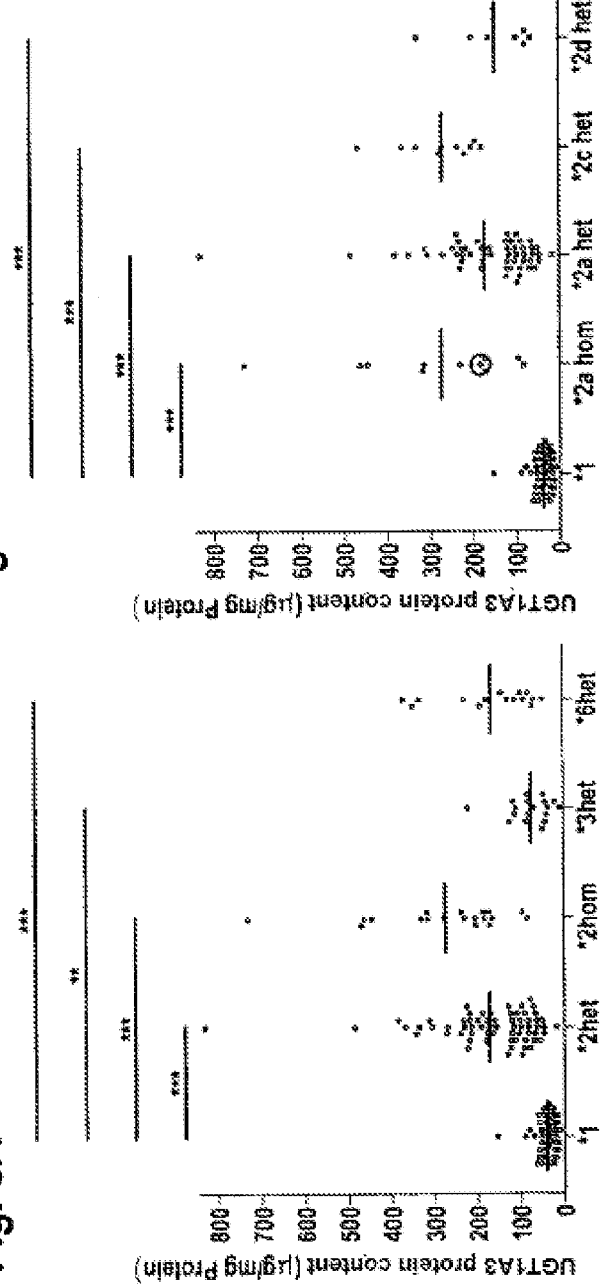

METHOD FOR DETERMINING THE PREDISPOSITION OF A PATIENT TO CHANGED BIOTRANSFORMATION AND TO THE DEVELOPMENT OF UNDESIRED DRUG EFFECTS IN A TREATMENT OF THE PATIENT WITH ATROVASTATIN

This application is a 35 U.S.C. §371 National Stage Application of PCT/EP2010/052245, filed on Feb. 23, 2010, which claims the benefit of priority to Serial No. DE 10 2009 015 978.9, filed on Mar. 26, 2009 in Germany, the disclosures of which are incorporated herein by reference in their entirety.

The present disclosure relates to a method for determining a predisposition of a patient to changed biotransformation and to the development of undesired drug effects in the treatment of the patient with statins as a result of a genetically determined change in the capacity for the biotransformation thereof.

BACKGROUND

Muscle diseases, such as for example myopathies and rhabdomyeloses, are diseases of the muscles which can for example be triggered by the administration of statins.

Statins, which include the active substance atorvastatin, are medicinal substances which are 3-hydroxy-3-methylglutaryl coenzyme A reductase (HMG CoA reductase) inhibitors. HMG CoA in turn is an intermediate of human cholesterol synthesis, because of which statins are mainly used as cholesterol lowering agents in fat metabolism disorders. Here, through the inhibition of HMG CoA reductase, the statins effect a lipid lowering in the blood. Since HMG CoA is a substance involved in the biosynthesis of cholesterol, less cholesterol is formed in the body under the action of statins than without the administration of statins. Inter alia, examples of the statins include atorvastatin, cerivastatin, fluvastatin, lovastatin, pravastatin, rosuvastatin and simvastatin.

Although statins are generally regarded as useful drugs, there are problems in the therapy, namely firstly as regards the uncertainty in the prediction of the effect corresponding to a certain dose, and secondly in the risk of the development of undesired drug effects (also abbreviated herein as "UDE" and generally also described as side-effects).

All statins, including atorvastatin, can cause undesired drug effects, among which the most severe are the so-called toxic myopathies, wherein there are structural and functional changes in the skeletal musculature. The most severe form of toxic myopathy is rhabdomyelosis, which inter alia manifest themselves in complete laming of all four limbs and can often take a fatal course. Up to the year 2003, ca. 3350 cases of rhabdomyelosis triggered by lipid lowering agents had been described in the literature.

Also, the strength of action of the various statins at present obtainable on the market is different; thus for example fluvastatin exhibits a low myopathy incidence, but on the other hand exhibits one of the weakest lipid lowering actions even at the maximum dosage.

As further undesired drug effects during the use of statins such as atorvastatin, liver damage, a decline in memory performance and alertness, as well as increased aggressivity and increased irritability have been observed, as well as headache, nausea, anemia, nerve damage, hair loss, and the like.

Since not all patients who are subjected to treatment with statins, in particular atorvastatin, for lowering the cholesterol content develop undesired drug effects, and patients react differently to certain statins, in particular atorvastatin, and the dosages thereof, it would be desirable to be able to determine, in advance of statin therapy, in particular atorvastatin therapy, the predisposition of a patient to develop undesired drug effects or to react other than as desired to the therapy.

SUMMARY

The purpose of the present disclosure is therefore to provide a method for determining a predisposition of a patient for the development of undesired drug effects or for altered efficacy in a treatment of the patient with statins.

According to the present disclosure, this problem is solved in that, in a biological sample from the patient the presence of at least one single nucleotide polymorphism (SNP) in the UGT1A3 gene (uridine diphosphate glucuronosyl transferase gene 1A3) and/or increased UGT1A3 gene expression is determined.

The problem on which the disclosure is based is fully solved in this manner.

In their own experiments on the basis of the study of many human liver samples, the inventors were able to show that genetic variations in the UGT1A3 gene led to increased UGT1A3 gene expression. Further, the inventors were able to show that the increased gene expression was accompanied by increased lactonization of the statin atorvastatin (ATV).

An increased content of ATV lactone is found in atorvastatin patients who suffer from a myopathy, and also increased concentrations of hydroxy metabolites of atorvastatin (see Hermann et al., "Exposure of atorvastatin is unchanged but lactone and acid metabolite are increased several-fold in patients with atorvastatin-induced myopathy", Clin. Pharmacol. Ther., 2006, 79: 532-539). Moreover, it has been demonstrated on a cell culture model that in comparison to the respective statin acids, statin lactones exhibit 14-37 fold increased myotoxicity (Skottheim et al., Statin induced myotoxicity: the lactone forms are more potent than the acid forms in human skeletal muscle cells in vitro; Eur. J. Pharm. Sci. 33: 317-25 (2008)).

It is known that in vivo atorvastatin is biotransformed inter alia into 2-(ortho) and 4-(para) hydroxy ATV acids (pharmacologically active metabolites). Alternatively, the free acid side-chain can be converted into cyclic ATV lactone. Owing to the higher lipophilicity of the ATV lactone, this is hydroxylated much more readily than ATV itself (see Jacobsen et al., Drug Metabol. Dispos. 28(11): 1369-78 (2000)). Thus with the present discoveries the inventors were able for the first time to show that the increased content of ATV lactone and of hydroxy ATV lactone is attributable to an increased activity of the enzyme uridine diphosphate glucuronosyl transferase, or rather to the increased activity of the isoform 1A3 of this enzyme triggered by the genetic variations.

The ATV lactonization can admittedly be catalyzed by several UGT isoforms (see for example Goosen et al.: "Atorvastatin glucoronidation is minimally and non-selectively inhibited by the fibrates Gemfibrozil, Fenofibrate and Fenofibric Acid", Am. Soc. Clinic. Pharma. Therap., 2007: 35(8) 1315-1323), however it was not previously known which of the isoforms assumes the main function in vivo. As already stated, UGTs (UDP glucuronosyl transferases) are enzymes which inter alia cause the lactonization of statins, for example atorvastatin. In turn, compared to the statins themselves, the lactonized statins are preferentially converted by the enzyme CYP3A into hydroxy-statin lactones.

Herein, the UGT1A3 gene is always understood to mean the coding sequence of this gene as well as the intron sequences and the 5'- and 3' untranslated/regulatory regions of the gene.

With the method now existing, it is for the first time possible to screen patients who are to undergo a statin treatment, in particular an atorvastatin treatment, or patients who are already undergoing a statin treatment, so as to determine whether they are genetically predisposed to increased activity of the isozyme UGT1A3, and thereby run the risk of forming more statin lactone and hydroxy statin lactone, which can lead to the abovementioned muscle diseases, or to a partial failure of therapy, since the statin lactones are pharmacologically inactive metabolites. Thus in this case or in these patients, atorvastatin very probably does not possess the same activity as is the case in patients who do not exhibit these polymorphisms. Advantageously, by the determination of the polymorphisms it can then directly be predicted whether atorvastatin is biotransformed to an increased extent and will thus be less effective at its dosage than in a patient who does not exhibit the polymorphisms; if polymorphisms according to the present disclosure are identified, either the actual or planned dosage of atorvastatin can be appropriately adapted, i.e. increased, in order to achieve a similar activity of atorvastatin as in wild type patients, or recourse can be had to another statin or another therapeutic approach in order to avoid undesired drug effects.

According to the present disclosure, this is effected by the determination of at least one SNP in the UGT1A3 gene. Thereby, the therapy of the patient to be treated with the statin can be individually tailored, i.e. either entirely different alternatives to the statins can be used, or else the dosage and hence the efficacy of certain statins to be administered can be individually considered for the patient.

As well as atorvastatin, other statins are at present also used, such as for example cerivastatin, fluvastatin, lovastatin, pravastatin, rosuvastatin and simvastatin.

Said statins are at present sold on the market for example under the names Sortis®, Lipitor® (atorvastatin), Baycol®, Zenas® (cerivastatin), Cranoc®, Lescol®, Locol®, Fractal® (fluvastatin), Mevinacor® (lovastatin), Mevalotin®, Pravasin®, Pravachol® (pravastatin), Crestor® (rosuvastatin), Gerosim®, Simvabeta®, Zocor® (simvastatin) and the corresponding generic forms thereof.

With the method now available, a targeted and individualized cholesterol synthesis inhibitor therapy can now advantageously be provided whereby the patients who have to undergo such a therapy can be examined for the presence of SNPs in the UGT1A3 gene either before or during the treatment with one of said drugs. If an SNP which leads to increased expression of this gene and hence to increased activity of the UDP glucuronyl transferase is present, the treatment can be performed or continued either with alternatives to the statins or with a statin other than that intended, or else with a dosage other than the original one or that originally intended.

In a further embodiment, it is preferred if at least one of the following haplotypes is determined in the method according to the disclosure: UGT1A3*2, UGT1A3*3, UGT1A3*6 and in particular one of the following SNPs in the UGT1A3 gene:
UGT1A3*2: rs55772651, rs1983023, rs56304713, rs45507691, rs3806597, rs3806596, rs3821242, rs6706232, rs6431625, rs17868336 and rs7574296;
UGT1A3*3: rs55772651, rs56304713, rs3806597, rs3806596, rs3821242, rs6706232 and rs7574296;
UGT1A3*6: rs55772651, rs1983023, rs56304713, rs3806597, rs3806596, rs3821242, rs6706232, rs6431625, rs7574296 and rs45449995.

Herein the expression "genomic Pos. in AF297093" is used to designate an SNP for which no rs number is available, the position whereof in the UGT1 gene locus which is designated with the access number AF297093 according to the publicly accessible databases is correspondingly stated (on the UGT1 gene locus see for example the EMBL EBI database under http://www.ebi.ac. uk/cgi-bin/expasyfetch?AF297093 or the database GenBank of the National Center for Biotechnology Information NCBI http://www.ncbi.nlm.nih.gov/).

SNPs (single nucleotide polymorphisms) designate variations of individual base pairs in a DNA strand compared to the wild type in a certain population. SNPs represent ca. 90% of all genetic variants in the human genome, and occur unequally strongly in certain regions in the genome. They are mutations, i.e. genetic changes, which have to a certain extent become established in the gene pool of a population. Also, the SNPs can occur as substitutions, in which a base, for example cytosine, is replaced by another base, for example thymine, or else as deletions or insertions.

Here, SNPs always have one of two or very rarely also several states and are allelically transmitted. The majority of the known SNPs affect non-coding regions in the genome, i.e. regions which lie either between genes or between exon regions of individual genes. In principle, these gene variants in non-coding regions can also affect regulatory sequences, e.g. promoters, enhancers or splicing sites and hence have effects on the expression of genes. SNPs which directly affect the coding sequence can be silent, i.e. the base substitution does not alter the translation of the corresponding triplet code into the analogous amino acid and hence thereby has no influence on the peptide sequence. However, because of different frequency of equivalent t-RNAs for specific base triplets, differences for the efficiency of the translation can arise and thus the expression of certain genes can be influenced post-transcriptionally by silent SNPs. Some SNPs have a coding function, i.e. the different alleles lead to the incorporation of a different amino acid into the resulting peptide, with the result that the function thereof can be changed.

In the genome, if they are present biallelically, SNPs can occur in three possible genotypes, namely in one of two homozygotic forms (allele 1/allele 1 or allele 2/allele 2) or else in one heterozygotic form (allele 1/allele 2). Adjacent SNPs can be linked together to a varying extent. That is, up to a certain percentage they arise in the population in a certain combination only together and thus form a so-called haplotype. Here, "coupling" is understood to mean the tendency that the alleles present each time at two different positions on one chromosome are passed on together (on the same chromosome), i.e. are transmitted coupled. In general here, with alleles that tend to be transmitted together the term "linkage disequilibrium" is used.

Since genomic DNA is double-stranded, each SNP can be identified with reference to each of the two strands. The SNPs preferred in the present application admittedly contain one substitution of one nucleotide by another at the polymorphic sites of the SNP, but SNPs can also be more complex and can have a deletion of a nucleotide from one, or an insertion of a nucleotide into, one of two corresponding sequences.

The expression "determine" as it is used herein for the determination of the SNPs, relates to various methods and processes for the analysis of one or more SNP at a certain site in the genome, and the expression also includes both direct determination, i.e. for example sequencing, and also indirect determination, i.e. for example amplification and/or hybridization.

The inventors have now discovered that, surprisingly, it is possible on the basis of certain SNPs in the UGT1A3 gene to diagnose a genetic predisposition for the development of muscle diseases or a changed efficacy in the administration of statins.

With the new method, it is now for the first time possible to prognosticate an individually probable exacerbation of a muscle disease on administration of atorvastatin or an individually probable lowered efficacy of atorvastatin.

Also, in a further embodiment it is preferred if the at least one SNP is selected from the SNPs which are in linkage disequilibrium with the SNPs of the UGT1A3*2, UGT1A3*3 and UGT1A3*6 haplotypes.

This means that in the context of the method according to the disclosure SNPs can also be detected which can likewise be used as markers of the haplotypes of the UGT1A3*2, UGT1A3*3 and UGT1A3*6, but are not explicitly listed here, but which are in linkage disequilibrium with the aforesaid SNPs (see for example Ménard V. et al., "Analysis of inherited genetic variations at the UGT1 locus in the French-Canadian population". Hum Mutat. 2009 Feb. 8).

In a further embodiment of the method according to the disclosure, it is preferred if the increased UGT1A3 gene expression is determined via an increased mRNA level and/or an increased protein level.

The proof provided by the inventors that the genetic variations in the UGT1A3 gene lead to increased UGT1A3 expression and hence also to increased activity of this enzyme is contrary to the knowledge previously obtained, albeit only by means of recombinant isoenzymes, according to which the genetic variations were as a rule associated with decreased function (see for example Chen et al., "Genetic Variants of Human UGT1A3: Functional Characterization and Frequency Distribution in a Chinese Han Population", Drug Metabolism and Disposition, 2006, 34: 1462-1467; Caillier et al., "A pharmacogenomics study of the human estrogen glucuronosyl transferase UGT1A3", Pharmacogenet. Genomics 2007, 17(7): 481-95).

Hence the present discoveries and the method provided, although admittedly UGT1A3 and UGT1A3 polymorphisms were already identified in the state of the art, are novel and surprising, since the polymorphisms were associated with decreased activity or expression of UGT1A3. However the inventors of the present application have now precisely found out that the polymorphisms are accompanied by higher UGT1A3 expression and as a result also increased activity, which, as described further above, leads to the increased ATV lactonization.

In particular in the process according to the disclosure it is preferred if for the detection of at least one SNP in the UGT1A3 gene an oligonucleotide is used which is selected from one of the oligonucleotides listed in Tables 1 and 2, or from the oligonucleotides with the SEQ ID Nos. 1 to 27:

TABLE 1

UGT1A3 amplification primers.

| SEQ-ID No. | Genomic position | Primer sequence (5'→ 3') | Ampl. product (bp) |
|---|---|---|---|
| 1 | 144852-145219 | ACGTTGGATGCCTGGATGACTGAAATAAAG | 388 |
| 2 | | ACGTTGGATGCAGCGTGGAGGCTGGCTATG | |
| 3 | 145477-145927 | ACGTTGGATGACTTGGATGTTCCCCAGAGT | 471 |
| 4 | | ACGTTGGATGCCTCTGGGGTGAGGACCACT | |
| 5 | 145934-146495 | ACGTTGGATGTGCACATCAAAGAAGAGAAC | 582 |
| 6 | | ACGTTGGATGACAGATGCATGACTGAGAAT | |
| 7 | 146519-146741 | ACGTTGGATGTGATGGACTACCCCAGGCCA | 243 |
| 8 | | ACGTTGGATGCTGAAGGCTATTATGACAAG | |

Here, the oligonucleotides with the SEQ ID Nos. 1, 3, 5 and 7 are forward ("f") primers and the oligonucleotides with the SEQ ID Nos. 2, 4, 6 and 8 reverse ("r") primers.

TABLE 2

Extension primers for the MALDI-TOF mass spectrometric analysis

| SEQ-ID No. | Assay | Genomic position | Primer sequence (5'→ 3') | Mass of the ampl. product (Da) |
|---|---|---|---|---|
| 9 | 1 | 144977 | CTCCCTGAACCCACC | 4417.9 |
| 10 | 2 | 144984 | CAAGACAACCCTAGCAA | 5141.4 |
| 11 | 1 | 145154 | GGATATTTCTTGTAAGGATCA | 6475.2 |
| 12 | 3 | 145182 | TGGTTTTGGTCGTTTTT | 5219.4 |
| 13 | 1 | 145531 | CCTGGAAAAGACCGATCA | 5501.6 |

TABLE 2-continued

Extension primers for the MALDI-TOF mass spectrometric analysis

| SEQ-ID No. | Assay | Genomic position | Primer sequence (5'→ 3') | Mass of the ampl. product (Da) |
|---|---|---|---|---|
| 14 | 1 | 145669 | TGCTACATTTGCTTTCTTC | 5710.7 |
| 15 | 3 | 145765 | CTGAGATGGCCACAGGACTCC | 6416.2 |
| 16 | 1 | 145751 | AGTCCTGTGGCCAGCC | 4858.2 |
| 17 | 1 | 145815 | ACCAACACCTTTCCACT | 5034.3 |
| 18 | 2 | 145874 | GCATGGAGCTCCCGCAAG | 5509.6 |
| 19 | 2 | 145968 | ACGAAATGGCATAGGT | 4954.3 |
| 20 | 3 | 146062 | ATTGCCATACTTCTGAAAA | 5770.8 |
| 21 | 1 | 146076 | GACATATTGTTCAACATTGC | 6091.0 |
| 22 | 3 | 146207 | CCGTTAACCTCTGCG | 4503.9 |
| 23 | 1 | 146211 | TCGACAGGTACTTAGCCAGCAC | 6704.4 |
| 24 | 1 | 146253 | GATTCCTACTGTGTTTTTTT | 6374.2 |
| 25 | 1 | 146271 | AGGAACATTCCATGTGA | 5218.4 |
| 26 | 1 | 146356 | CAACCAATTCAGACCACATGACATTC | 7852.1 |
| 27 | 1 | 146542 | TACCCCAGGCCAATC | 4481.9 |

Genomic (gen.) position corresponding to the file with the GenBank access number (Acc. Number) AF297093.1.

With these oligonucleotides, the inventors were successfully able to amplify the regions containing the SNPs and to identify the SNPs via the extension of these oligonucleotides (primers). Hence the present disclosure also relates to these oligonucleotides themselves.

In a further embodiment it is preferred if at least one of the following methods is used for the determination of the at least one SNP: PCR-based methods, DNA sequencing methods, hybridization methods, mass spectroscopy, HPLC methods and primer extension methods.

These methods are adequately known in the state of the art and are already used for the identification of SNPs. For example reference is hereby made to "Guide to Mutation Detection" by Graham R. Taylor and Ian N. M. Day (Wiley & Sons, 2005) in which these methods are adequately described.

In a further embodiment it is preferred if the following PCR cycles are used for the amplification of the SNP containing regions.

Denaturation at ca. 95° C. for 15 mins, followed by 5 cycles with the steps ca. 95° C. for 20 secs, ca. 65° C. for 30 secs and ca. 72° C. for 1 min; followed by 40 cycles with the steps ca. 95° C. for 20 secs, ca. 62° C. for 30 secs and ca. 72° C. for 1 min, followed by a final extension step at ca. 72° C. for 10 mins.

Further, the disclosure also relates to diagnostic kits for the determination of a predisposition of a patient for the development of muscle diseases in a treatment of the patient with statins, wherein the kit contains at least one oligonucleotide as described above.

With the kit according to the disclosure a simple tool is provided with which at least one relevant SNP in the UGT1A3 gene and can be rapidly detected, whereby patients can be identified who will with high probability develop muscle diseases as a side-effect during a therapy with a statin.

The disclosure further relates to the use of at least one SNP in the human UGT1A3 gene, in particular the SNPs rs55772651, rs1983023, rs56304713, rs45507691, rs3806597, Rs3806596, rs3821242, rs6706232, rs6431625, rs17868336, rs7574296, g.146356 (gen. Pos. In Af297093) and rs45449995 and also other SNPs which are in linkage disequilibrium with the UGT1A3*2, UGT1A3*3 and UGT1A3*6 haplotypes for the determination of the predisposition of a patient to the development of muscle diseases during the treatment of statins.

Further advantages and features of the disclosure emerge from the following description and the attached diagrams.

It goes without saying that the features stated above and features yet to be explained below are usable not only in the combination stated in each case, but also in other combinations or alone, without departing from the scope of the present disclosure.

BRIEF DESCRIPTION OF THE DRAWINGS

In the diagrams,

FIG. 4 shows a schematic overview of the structure of the UGT1A3 haplotypes in the human liver;

FIG. 5 shows the genotype-phenotype correlation for UGT1A3-mRNA;

FIG. 6 shows the genotype-phenotype correlation for UGT1A3-protein; and

DETAILED DESCRIPTION

Figure 1:
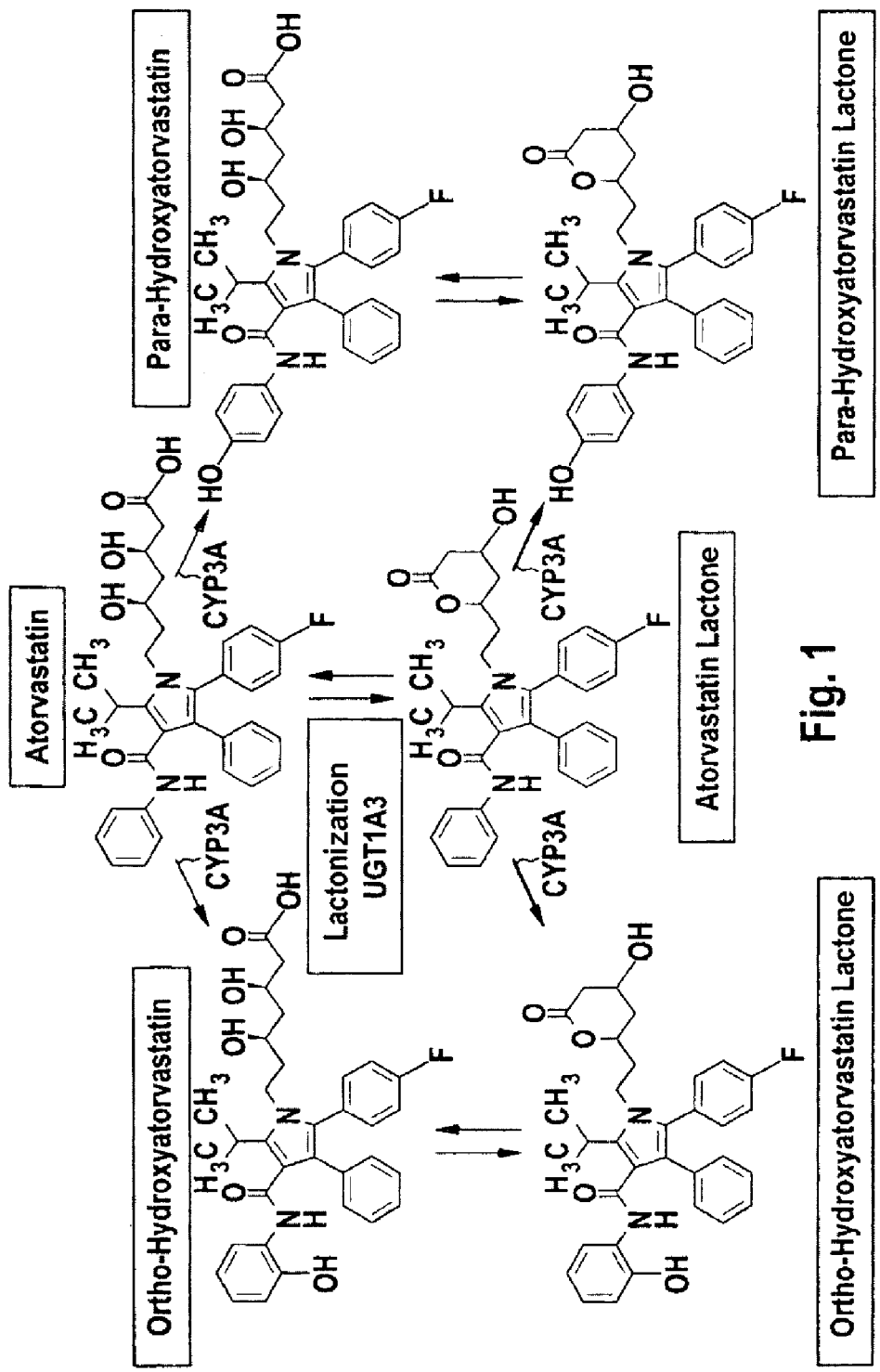
FIG. 1 shows an overview of the biotransformation of the statin atorvastatin in the human body.

FIG. 1 shows a schematic overview of the metabolism of the statin atorvastatin, the structural formula of which is shown below the name. "HMGCR" is the abbreviation for the enzyme 3-hydroxy-3-methylglutaryl coenzyme A reductase (HMG CoA reductase), which is inhibited by the statins.

From the diagram it can be inferred that the enzyme UGT (and, as the inventors were able to demonstrate, mainly UGT1A3) is responsible for the lactonization of atorvastatin (ATV) to ATV lactone (lower diagram edge, in center).

Further, it is shown in the diagram that enzymes of the cytochrome P450 subfamily CYP3A (these are above all CYP3A4 and CYP3A5) catalyzes the hydroxylation of atorvastatin either to 2- or to 4-hydroxy atorvastatin, but less effectively than the hydroxylation of ATV lactone (indicated by the different thicknesses of the arrows indicating the reaction).

Figure 2A:
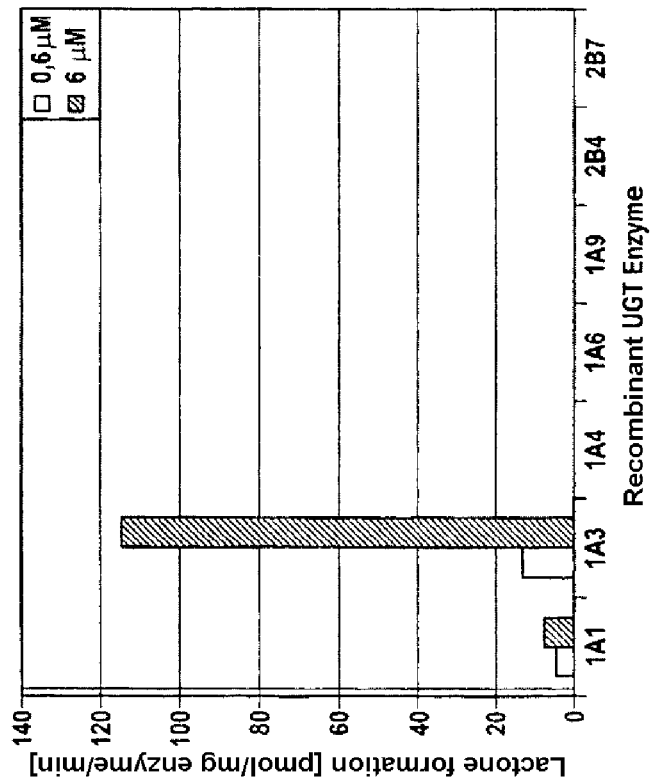
FIG. 2 shows diagrams relating to the activities of the various UGT isoenzymes, according to which the isoenzyme 1A3 displays the highest activity as regards the ATV lactonization.
Figure 2B:
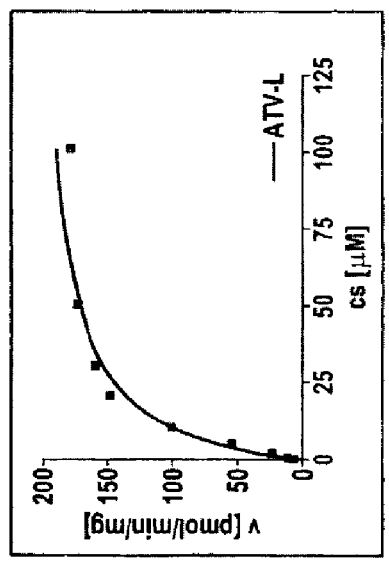
Figure 2C:
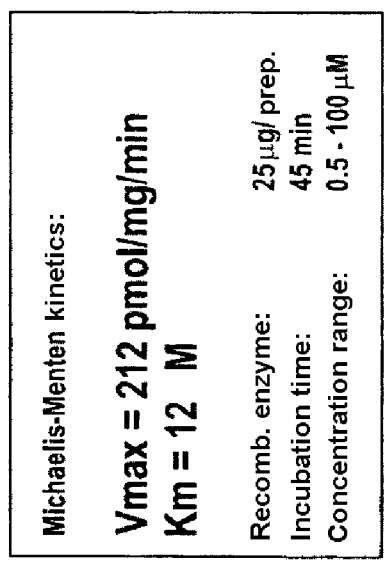

FIG. 2 shows in a bar chart (on left; 2A) the measured enzyme activities of the various recombinant UGT isoenzymes at two different substrate concentrations (0.6 μM, white bars, and 6 μM, black bars). According to this, only the isoenzymes 1A1 and 1A3 have a measurable activity as regards the ATV lactonization, and UGT1A3 shows by far the higher activity at higher substrate activity. The kinetic parameters Michaelis-Menten constant Km and maximal activity Vmax were determined with recombinant UGT1A3 enzyme by measurements of the lactonization activity (v) at different substrate concentrations (cs) (on right; 2B), and the test preparations and the result for Vmax are shown in FIG. 2C.

Figures 3A, 3B, 3C:
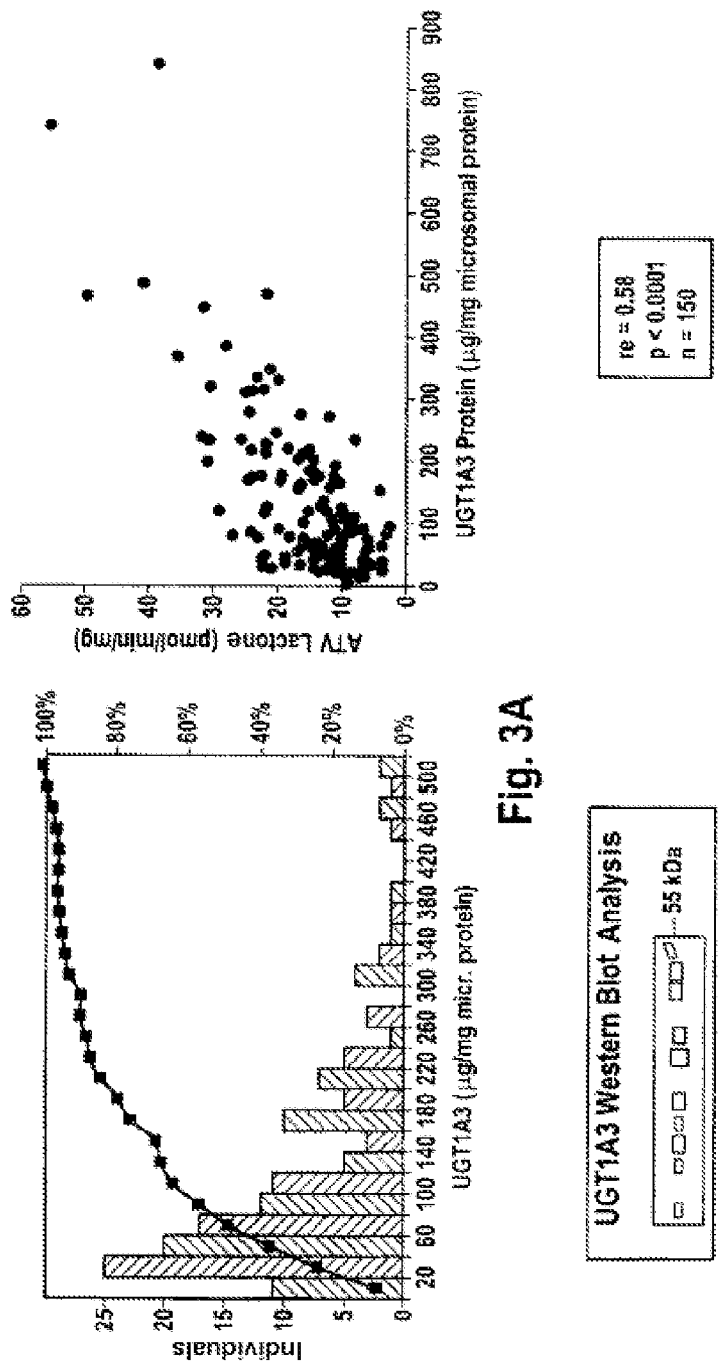
FIG. 3 shows diagrams on the distribution of the UGT1A3 protein in patient samples and correlation of the activity of the atorvastatin lactonization (on right) to the protein content in the human liver.

FIG. 3 shows on the left (FIG. 3A) a histogram on the distribution of the UGT1A3 protein in the population random survey of 150 liver samples in the IKP liver bank. Below the histogram by way of example, a Western blot analysis is shown (FIG. 3B). The 55 kDa protein band labeled by the specific antibody was seen as a double band, which was caused by glycosylation of the protein. The rising curve in the histogram indicates the cumulative frequency and the curved brackets indicate possible subgroups with increased activity. In the right-hand diagram (FIG. 3C), the correlation of the atorvastatin lactonization to the protein measurements in the human liver is shown. The correlations were statistically assessed. In the box below the diagram, the Spearman rank correlation coefficient $r_s$ and the statistical significance as the p-value is given.

FIG. 4 shows an overview of the structure of the UGT1A3 gene with the approximate position of the mutations studied in the liver samples (grey: promoter region; white: silent mutations in the coding region; black: amino acid substitutions) relative to the exons (black boxes 1-5). Thereunder are shown the UGT1A3 haplotypes and haplotype variants which were identified in the studies in the human liver samples. For this, DNA samples belonging to the liver samples were genotyped by the UGT1A3 genotyping method. The SNP data (stated in the upper region with genomic position and/or rs number) were then analyzed with the program Phase (version 2.1). In the lower region, the base belonging to each position studied is stated.

FIG. 5 shows the correlation between genotype and phenotype for UGT1A3 mRNA in the human liver samples studied (n=150). The left-hand diagram (FIG. 5A) shows which mRNA value is exhibited by each liver sample of a certain genotype. The right-hand diagram (FIG. 5B) shows the mRNA values of the different UGT1A3*2 haplotype variants. Significant differences were determined by means of the "Mann Whitney test".

FIG. 6 shows the correlation between genotype and phenotype for UGT1A3 protein in the microsomal fractions of the human liver samples studied (n=150). The left-hand diagram (FIG. 6A) shows which UGT1A3 protein value is exhibited by each liver sample of a certain genotype. The right-hand diagram (FIG. 6B) shows the protein values of the different UGT1A3*2 haplotype variants. Significant differences were determined by means of the "Mann Whitney test".

Figure 7A:
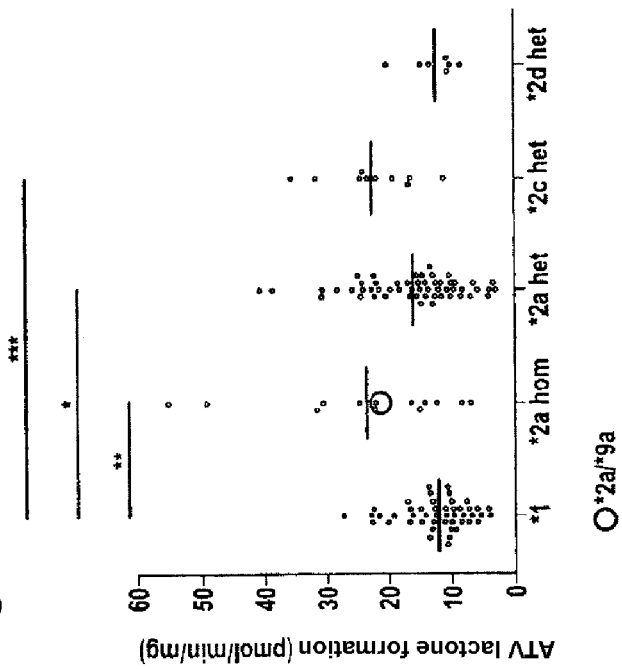
FIG. 7 shows the genotype-phenotype correlation for UGT1A3-lactonization activities.
Figure 7B:
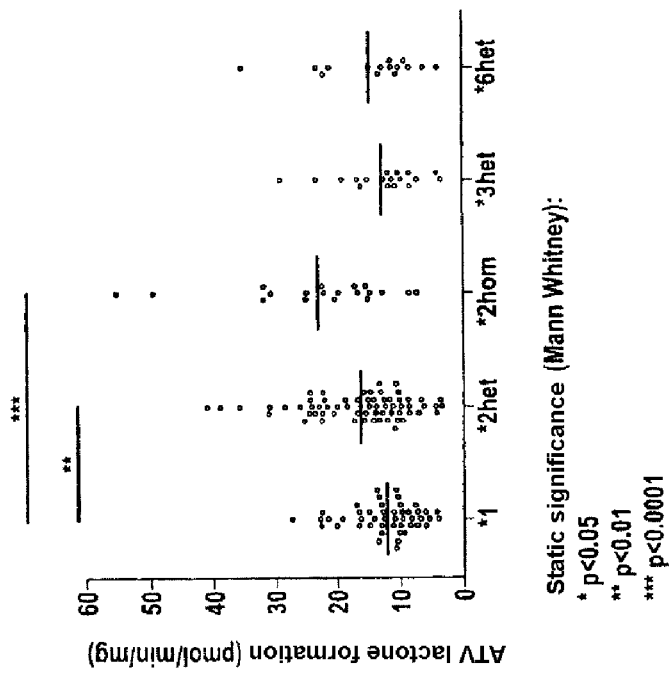

FIG. 7 shows the correlation between genotype and phenotype for the atorvastatin lactonization in the microsomal fractions of the human liver samples studied (n=150). The left-hand diagram (FIG. 7A) shows which mRNA value is exhibited by each liver sample of a certain genotype. The right-hand diagram (FIG. 7B) shows the mRNA values of the different UGT1A3*2 haplotype variants. Significant differences were determined by means of the "Mann Whitney test".

Material and Methods

Patient DNA and Liver Samples

Liver tissue and corresponding blood samples belong to a human liver bank built up at the IKP Stuttgart. The samples were obtained in 1999-2000 from patients who had undergone a surgical operation on the liver for medical reasons (described in Wolbold et al: Sex is a major determinant of CYP3A4 expression in human liver; *Hepatology* 2003, 38: 978-988). All tissue samples were examined by a pathologist and it was thereby ensured that only histologically normal tissue was used. The clinical patient documentation was completely anonymized and contains information on the sex, age, medical diagnosis, drug therapy, alcohol and smoking habits, and certain laboratory values. Samples from patients with hepatitis, cirrhosis or chronic alcohol abuse were excluded. A total of 150 liver samples, from which high quality RNA and complete documentation were available, were used for these studies. The liver microsomes used for Western blot and enzyme activity measurements were prepared by standard methods (described in Lang et al.: Extensive genetic polymorphism in the human CYP2B6 gene with impact on expression and function in human liver; *Pharmacogenetics* 2001, 11: 399-415). Genomic DNA for genotype studies was isolated from blood samples of the respective tissue donors. Appropriate approval for the studies was obtained from the local ethics committee. The studies were performed in accordance with the Helsinki Declaration and all patients had given their written consent.

Determination of the UGT1A3 mRNA

Total RNA was prepared from liver tissue using the RNeasy Midi Kit (Qiagen, Hilden, Germany). The UGT1A3 mRNA was quantified by means of an in-house developed, specific TaqMan real time reverse transcription PCR assay on a 7900HT Fast Real Time PCR system (Applied Biosystems, Foster City, Calif.). For this, a primer pair 1A3_tq_new_f/r spanning the Intron1 (see Table 3 below) and the FAM-labeled UGT1A3 MGB probe were used at respective concentrations of 400 nmol/l and 200 nmol/l. Cross-reactions against UGT1A4 were excluded by testing DNA plasmids of both genes as templates (data not shown). The PCR reaction preparations contained 2× universal PCR Master Mix (Applied Biosystems) in a final volume of 12.5 µl and the following PCR cycle conditions were used: 50° C. for 2 mins; 95° C. for 10 mins, followed by 40 cycles with the steps 95° C. for 15 secs and 60° for 1 min.

TABLE 3

Amplification primers for the quantitative PCR

| SEQ-ID No. | c. position | Primer sequence (5'→ 3') | Amplification product (bp) |
|---|---|---|---|
| 28 | 347-371 | TGTTGAACAATATGTCTTTGGTCTA | 698 |
| 29 | 258-278 | GAAGGAATTTGATCGCGTTAC | 787 |
| 30 | 171-189 | GGTGGTGGTCCTCACCCTG | 874 |
| 31 | 1024-1044 | GTTCGCAAGATTCGATGGTCG | |
| 32 | 738-763 | GGATATTCTCAGTCATGCATCTGTGT | 297 |
| 33 | 1017-1034 | TTCGATGGTCGGGTTCCA | |
| 34 | 795-807 | 6FAM-CCCCAGGCCAATC-MGB | |

The positions corresponding to cDNA sequences ("c. position") with the GenBank access numbers (Acc. numbers) CCDS2509.1 (UGT1A3), CCDS33405.1 (UGT1A4) and CCDS33404.1 (UGT1A5).

Determination of the Microsomal UGT1A3 Protein Content

The UGT1A3 protein was quantified by Western blot analyses of 150 liver samples. As the primary antibody, a monoclonal antibody (ab57400 from abcam) was used. As the secondary antibody, goat anti-mouse IRDye 800CW (LICOR Biosciences) was used, and the detection was effected by means of the ODYSSEY infrared imaging system (LICOR Biosciences). 20 µg of human liver microsomes were subjected to an SDS-PAGE (10% SDS separation gels) and blotted onto nitrocellulose membranes. The blots were incubated with 3 µg/ml anti-UGT1A3 in 1% skimmed milk/TBST for 2 hours, and the incubation with the secondary antibody, diluted 1:10,000 in 1% skimmed milk (TBST), was then performed for 30 minutes.

The Western blots gave three bands at ca. 55 kDa for the recombinant UGT1A3s and two bands for UGT1A3 from liver. After deglycosylation of the samples, one band remained in both cases. For the quantification in the liver microsomes, the intensity of the bands was combined.

The relative quantification was performed by means of the ODYSSEY software against a standard curve (5 points; 0.5-8 µg) recombinant UGT1A3 (human UGT1A3 supersomes; BDBiosciences, catalog number 456413). The results from different blots were normalized to results on pooled microsomes which were used for every blot.

The specificity of the antibodies was tested against 10 µg of recombinant UGT1A1, 1A4, 1A6, 1A9, 2B4 and 2B9. Regarding UGT1A6, 1A9, 2B4 and 2B9, no cross-reactivity could be found; against UGT1A1 and 1A4 at maximum sensitivity a slight cross-reactivity was discernible, which did not however affect the data assessment.

Determination of the UGT1A3 Activity for Atorvastatin Lactonization

For the measurement of the atorvastatin lactone formation by human liver microsomes, an LC-MS assay was established: for this, 25 µg of microsomes are preincubated for 10 minutes at 37° C. in 50 mM Tris HCl, pH 7.4 with 5 mM magnesium chloride, 25 µg/ml alamethicin and 10 µM atorvastatin in a total volume of 100 µl. The reaction is started by addition of 10 mM UDP glucuronic acid, the cosubstrate of the UDP glucuronosyl transferases (UGT). The samples were incubated for 30 minutes. The reaction was stopped by addition of 25 µl of ice-cold 250 mM formic acid in acetonitrile and the vortexed samples were immediately placed on ice. In order to be able to monitor the LC/MS quantification, 10 µl of internal standard was added to the 100 µl samples. The samples were centrifuged for 5 minutes at 13,000 rpm and placed in glass vessels for the LC/MS measurement.

With the LC/MS method, atorvastatin, atorvastatin lactone and the para- and ortho-hydroxy forms can be quantified together in the 5 nM to 5 µM range. The samples are separated on an XBridge Shield RP18 3.5 µm column with a C8 precolumn with a 1 mM formic acid and acetonitrile gradient for 23 minutes at 30° C. The masses are detected by HCT Esquire plus mass spectrometer, this being after electrospray ionization of the substances separated by the column.

Genetic Analyses at the UGT1A Locus

Caillier et al (2007) detected 7 promoter and 13 exon-1 SNPs (4 synonyms) in 249 patient samples by sequencing. The UGT1A family differs only in exon 1 and has identical exons 2 to 5. The present approach consisted in establishing a method for detecting these described 18 promoter and exon-1 SNPs plus 1 frameshift SNP in exon 1 (rs45586035). Four regions which contain these SNPs were amplified by means of Qiagen Hotstar polymerase in 10 ng of genomic DNA with primers which were specifically constructed for the amplification of only UGT1A3. All MALDI-TOF MS amplification primers (see Table 1 above) had a 5' "tag" sequence (ACGTTGGATG) to enable more efficient amplification (recommendation of the software MassArray Assay Design (v.3.0.0)). A specific PCR protocol was used in order to ensure a high specificity, and in order to achieve a high yield: Multiplex PCR preparations in 384-well microtiter plates, volume 5 µl, contained 10 ng of predried DNA, 4 µl of "HotstarTaq Master Mix" with HotstarTaq polymerase (Qiagen GmbH, Hilden, Germany), 0.1 µM of each amplification primer (see Table 1 above) and 0.5 mM $MgCl_2$ (Qiagen). The PCR conditions (Gene Amp PCR System 9700, Applied Biosystems, Foster City, Calif.) were as follows: denaturation at 95° C. for 15 mins, followed by 5 cycles with the steps 95° C. for 20 secs, 65° C. for 30 secs and 72° C. for 1 min; followed by 40 cycles with the steps 95° C. for 20 secs, 62° C. for 30 secs and 72° C. for 1 min; followed by a final extension step at 72° C. for 10 mins. In order to confirm the specificity, these fragments were sequenced in one sample, and the PCR products of some samples were constantly tested on agarose gels as regards correct amplification and with contamination-free water controls.

After amplification of these fragments, excess dNTPs were dephosphorylated in a final volume of 7 µl with 0.3 µl of SAP (1.7 U/µl) in 0.17 µl of 10×SAP buffer (Sequenom, San Diego, Calif.) and 1.53 µl of water at 37° C. for 20 mins, followed by 10 mins at 85° C. and 20° C. for 1 sec.

Specific primers were devised which end directly before SNP positions (see Table 2 above). In the amplification step, they were each elongated by only one labeled base which matches the SNP base. The primer of one assay was devised such that the products thereof differ in mass by at least 15 Da. The detectable masses lay in the range from 3000 to 8500 Da.

A specific amplification protocol, together with the iPlex enzyme and specific buffer conditions, were used for this step:

After addition of 0.2 µl of iPLEX buffer, 0.2 µL of iPLEX Terminator Mix and 0.041 µl of iPLEX enzyme (iPLEX Gold Reaction Kit, Sequenom), 0.0112 or 00224 µl of Extension Primer (500 µM) were added, depending on whether the primer mass was lower or higher than 6000 Da, in order optimally to adjust the signal-noise ratio. The conditions of the extension reaction were as follows: 94° C. for 30 secs, followed by 40 cycles with the steps 94° C. for 5 secs, with 5 subcycles of 52° C. for 5 secs and 80° C. for 5 secs; and a final extension step at 72° C. for 3 mins.

In order to avoid interfering sodium and potassium adducts, the samples were desalted by adding 6 mg of Clean Resin (Sequenom) and 16 µl of water in each case. After 20 mins incubation at room temperature, they were centrifuged for 20 mins at 4000 rpm. The samples were then applied onto 384 SpectroCHIP® arrays (Sequenom) using a nanodispenser and analyzed in the MassArray™ compact mass spectrometer (Sequenom). Automated spectrum recording was effected with the software Spectroacquire and data analysis with MassArray Typer software v.3.4. Samples not automatically assigned were subsequently analyzed manually.

Statistical and Computer-Assisted Analysis

The assessment of the genetic data was performed by means of publicly available programs. Observed and expected allele and genotype frequencies in the liver bank population were tested for deviations from the Hardy-Weinberg equilibrium by means of the DeFinetti program available on-line (Strom T M and Wienker T F, DeFinetti Program homepage for Hardy-Weinberg equilibrium test; http://ihg.gsf.de/cgi-bin/hw/hwa1.pl). Haplotype calculations were performed using the PHASE program, version v2.1.1. (The Matthew Stephens homepage; http://stephenslab.uchicago.edu/home.html) and using Haploview v.3.32 (The Broad Institute haploview homepage; http://www-.broad.mit.edu/mpg/haploview/).

Statistical analyses were performed with the statistics program Prism 4, version 4.03 (GraphPad Software Inc.). Spearman rank correlation coefficients were determined for the correlation analysis of the mRNA, protein and activity data. Haplotype group differences were determined by the "Mann Whitney test" (non-parametric T-test). All statistical tests were performed two-sided and statistical significance was defined as P<0.05.

Results

Using LC-MS/MS analysis, the role of individual recombinantly expressed CYP and UGT enzymes in the ATV hydroxylation and ATV lactonization was studied. Using a large bank for human liver tissue with 150 well-documented surgical liver samples, it was thereby possible to identify the UGT isoenzyme which is mainly responsible for the ATV lactonization in the liver. Further, genetic analyses were performed in order to identify SNPs and haplotypes of the relevant UGT genes which are responsible for ATV biotransformation.

Identification of CYP3A4 as Main Enzyme for the ATV Hydroxylation

Among the most important drug-metabolizing CYP enzymes, the cytochrome P450 CYP3A subfamily with the two isoenzymes CYP3A4 and CYP3A5 is the only relevant P450 enzymes which catalyze the ATV hydroxylation. The catalytic activity of CYP3A4 was intensified many times in comparison to the coexpressed cytochromes b5, cytochrome b5 being a known catalytic intensifier of CYP3A4 biotransformations.

Identification of UGT1A3 as Main Enzyme for the ATV Lactonization

FIG. 2A shows that among various recombinant UGT enzymes, UGT1A3 is the enzyme with the highest specific activity for the catalysis of the ATV lactonization. In contrast, UGT1A1 possessed only low activity. For recombinant UGT1A3, the kinetic analysis gave a Km value of 12 µM for the formation of the atorvastatin lactone (FIGS. 2B and C).

UGT1A3 protein data from 150 liver samples showed a 530-fold variability and a non-normal distribution, and the possible presence of subgroups with higher activity (see FIG. 3A). The microsomal UGT1A3 lactonization activity showed a 20-fold variability within the 150 liver samples. The lactonization correlated well with the UGT1A3 Western blot protein data (see FIG. 3B) and also with the quantitative UGT1A3 mRNA data of the real time PCR analysis (rs=0.38; P<0.0001; data not shown).

Genetic Analyses

A selection of SNPs of the UGT1A locus was determined in the DNA samples corresponding to the liver samples (n=19, see FIG. 4) by means of MALDI-TOF assays. In addition the UGT1A1 genotype was determined separately. There is a linkage disequilibrium between the SNPs, as could be shown by means of Haploview. The linkage is such that carriers of the UGT1A1*28 allele are in most cases also carriers of the UGT1A3*2 allele, i.e. the increased lactonization capacity of atorvastatin caused by increased UGT1A3 expression is also predictable by genotyping for UGT1A1*28.

Analyses for the correlation of the genotype with the phenotype for UGT1A3 at the levels mRNA, protein and atorvastatin lactonization are shown in FIGS. 5 to 7. UGT1A3*2, *3 and *6 haplotypes were the most widespread variants of the haplotypes. All three haplotypes exhibited significantly increased UGT1A3 protein expression (see FIG. 5). The activity for ATV lactonization was increased twofold in homozygotic *2 carriers compared to the wild type samples. The carriers of *3 and *6 haplotypes exhibited no increased lactone formation. Here it should be taken into account that the sample number was smaller than with the *2 carriers and that only heterozygotic carriers could be identified. Hence in homozygotic carriers, an effect on the enzyme activity might be measureable. The data in the present FIGS. 5-7 thus clearly show that the variants are associated with increased function.

The invention claimed is:

1. A method of treating a patient diagnosed with elevated cholesterol levels and being treated with atorvastatin comprising:
   assaying a biological sample from the patient;
   detecting in the biological sample one or more haplotype of a UGT1A3 gene (uridine diphosphate glucuronosyl transferase gene 1A3), wherein the one or more haplotype is selected from the group consisting of: UGT1A3*2, UGT1A3*2a, UGT1A3*2c, and UGT1A3*2d, and the patient possesses at least one of the one or more haplotype;
   after the detecting in the biological sample the one or more haplotype of the UGT1A3 gene, discontinuing treatment with atorvastatin; and
   after the discontinuing treatment with atorvastatin, administering one or more drugs, other than atorvastatin, for the treatment of elevated cholesterol levels.

2. The method as claimed in claim 1, wherein the one or more drugs other than atorvastatin comprises at least one statin selected from the group consisting of: fluvastatin, lovastatin, pravastatin, rosuvastatin, and simvastatin.

3. The method as claimed in claim 1, wherein the one or more haplotype is detected by assaying the biological sample for alleles of at least one single nucleotide polymorphism (SNP) located in the UGT1A3 gene and wherein the at least one SNP is selected from the group consisting of: rs55772651, rs1983023, rs56304713, rs45507691, rs3806597, rs3806596, rs3821242, rs6706232, rs6431625, rs17868336, and rs7574296.

4. The method as claimed in claim 1, further comprising assaying the biological sample to detect whether the patient possesses haplotype UGT1A1*28, UGT1A3*3, or UGT1A3*6.

5. The method as claimed in claim 1, wherein the one or more haplotype is detected using one or more oligonucleotide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

6. The method as claimed in claim 1, wherein the detection of the one or more haplotype comprises using one or more of the following methods: PCR-based methods, DNA sequencing methods, hybridization methods, mass spectroscopy, HPLC methods, and primer extension methods.

7. A method of treating a patient diagnosed with elevated cholesterol levels and not being treated with atorvastatin comprising:
   assaying a biological sample from the patient;
   detecting in the biological sample one or more haplotype of a UGT1A3 gene (uridine diphosphate glucuronosyl transferase gene 1A3), wherein the one or more haplotype is selected from the group consisting of: UGT1A3*2, UGT1A3*2a, UGT1A3*2c, and UGT1A3*2d, and the patient possesses at least one of the one or more haplotype; and
   after the detecting in the biological sample the one or more haplotype of the UGT1A3 gene, administering one or more drugs, other than atorvastatin, for the treatment of elevated cholesterol levels.

8. The method as claimed in claim 7, wherein the one or more drugs other than atorvastatin comprises at least one statin selected from the group consisting of: fluvastatin, lovastatin, pravastatin, rosuvastatin, and simvastatin.

9. The method as claimed in claim 7, wherein the detection of the one or more haplotype comprises using one or more of the following methods: PCR-based methods, DNA sequencing methods, hybridization methods, mass spectroscopy, HPLC methods, and primer extension methods.

10. The method as claimed in claim 7, wherein the one or more haplotype is detected by assaying the biological sample for alleles of at least one single nucleotide polymorphism (SNP) located in the UGT1A3 gene, and wherein the at least one SNP is selected from the group consisting of: rs55772651, rs1983023, rs56304713, rs45507691, rs3806597, rs3806596, rs3821242, rs6706232, rs6431625, rs17868336, and rs7574296.

11. The method as claimed in claim 7, further comprising assaying the biological sample to detect whether the patient possesses haplotype UGT1A1*28, UGT1A3*3, or UGT1A3*6.

12. The method as claimed in claim 7, wherein the one or more haplotype is detected using one or more oligonucleotide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

13. A method of treating a patient diagnosed with elevated cholesterol levels and being treated with an initial daily dose of atorvastatin comprising:
   assaying a biological sample from the patient;
   detecting in the biological sample to detect one or more haplotype of a UGT1A3 gene (uridine diphosphate glucuronosyl transferase gene 1A3), wherein the one or more haplotype is selected from the group consisting of: UGT1A3*2, UGT1A3*2a, UGT1A3*2c, and UGT1A3*2d, and the patient possesses at least one of the one or more haplotype; and
   after the detecting in the biological sample the one or more haplotype of the UGT1A3 gene, administering an adjusted, therapeutically effective daily dose that is increased from the initial daily dose of atorvastatin.

14. The method as claimed in claim 13, wherein the one or more haplotype is detected by assaying the biological sample for alleles of at least one single nucleotide polymorphism (SNP) located in the UGT1A3 gene, and wherein the at least one SNP is selected from the group consisting of: rs55772651, rs1983023, rs56304713, rs45507691, rs3806597, rs3806596, rs3821242, rs6706232, rs6431625, rs17868336, and rs7574296.

15. The method as claimed in claim 13, further comprising assaying the biological sample to detect whether the patient possesses haplotype UGT1A1*28, UGT1A3*3, or UGT1A3*6.

16. The method as claimed in claim 13, wherein the one or more haplotype is detected using one or more oligonucleotide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

17. The method as claimed in claim 13, wherein the detection of the one or more haplotype comprises using one or more of the following methods: PCR-based methods, DNA sequencing methods, hybridization methods, mass spectroscopy, HPLC methods, and primer extension methods.

* * * * *

SEQUENCE LISTING

<160> NUMBER OF SEQ ID NOS: 34

<210> SEQ ID NO 1
<211> LENGTH: 30
<212> TYPE: DNA
<213> ORGANISM: Artificial Sequence
<220> FEATURE:
<223> OTHER INFORMATION: Amplification Primer

<400> SEQUENCE: 1
acgttggatg cctggatgac tgaaataaag                               30

<210> SEQ ID NO 2
<211> LENGTH: 30
<212> TYPE: DNA
<213> ORGANISM: Artificial Sequence
<220> FEATURE:
<223> OTHER INFORMATION: Amplification Primer

<400> SEQUENCE: 2
acgttggatg cagcgtggag gctggctatg                               30

<210> SEQ ID NO 3
<211> LENGTH: 30
<212> TYPE: DNA
<213> ORGANISM: Artificial Sequence
<220> FEATURE:
<223> OTHER INFORMATION: Amplification Primer

<400> SEQUENCE: 3
acgttggatg acttggatgt tccccagagt                               30

<210> SEQ ID NO 4
<211> LENGTH: 30
<212> TYPE: DNA
<213> ORGANISM: Artificial Sequence
<220> FEATURE:
<223> OTHER INFORMATION: Amplification Primer

<400> SEQUENCE: 4
acgttggatg cctctggggt gaggaccact                               30

<210> SEQ ID NO 5
<211> LENGTH: 30
<212> TYPE: DNA
<213> ORGANISM: Artificial Sequence
<220> FEATURE:
<223> OTHER INFORMATION: Amplification Primer

<400> SEQUENCE: 5
acgttggatg tgcacatcaa agaagagaac                               30

<210> SEQ ID NO 6
<211> LENGTH: 30
<212> TYPE: DNA
<213> ORGANISM: Artificial Sequence
<220> FEATURE:
<223> OTHER INFORMATION: Amplification Primer

<400> SEQUENCE: 6
acgttggatg acagatgcat gactgagaat                               30

<210> SEQ ID NO 7
<211> LENGTH: 30
<212> TYPE: DNA
<213> ORGANISM: Artificial Sequence

```
<220> FEATURE:
<223> OTHER INFORMATION: Amplification Primer

<400> SEQUENCE: 7
acgttggatg tgatggacta ccccaggcca                                    30

<210> SEQ ID NO 8
<211> LENGTH: 30
<212> TYPE: DNA
<213> ORGANISM: Artificial Sequence
<220> FEATURE:
<223> OTHER INFORMATION: Amplification Primer

<400> SEQUENCE: 8
acgttggatg ctgaaggcta ttatgacaag                                    30

<210> SEQ ID NO 9
<211> LENGTH: 15
<212> TYPE: DNA
<213> ORGANISM: Artificial Sequence
<220> FEATURE:
<223> OTHER INFORMATION: Extension Primer

<400> SEQUENCE: 9
ctccctgaac ccacc                                                    15

<210> SEQ ID NO 10
<211> LENGTH: 17
<212> TYPE: DNA
<213> ORGANISM: Artificial Sequence
<220> FEATURE:
<223> OTHER INFORMATION: Extension Primer

<400> SEQUENCE: 10
caagacaacc ctagcaa                                                  17

<210> SEQ ID NO 11
<211> LENGTH: 21
<212> TYPE: DNA
<213> ORGANISM: Artificial Sequence
<220> FEATURE:
<223> OTHER INFORMATION: Extension Primer

<400> SEQUENCE: 11
ggatatttct tgtaaggatc a                                             21

<210> SEQ ID NO 12
<211> LENGTH: 17
<212> TYPE: DNA
<213> ORGANISM: Artificial Sequence
<220> FEATURE:
<223> OTHER INFORMATION: Extension Primer

<400> SEQUENCE: 12
tggttttggt cgttttt                                                  17

<210> SEQ ID NO 13
<211> LENGTH: 18
<212> TYPE: DNA
<213> ORGANISM: Artificial Sequence
<220> FEATURE:
<223> OTHER INFORMATION: Extension Primer

<400> SEQUENCE: 13
cctggaaaag accgatca                                                 18
```

<210> SEQ ID NO 14
<211> LENGTH: 19
<212> TYPE: DNA
<213> ORGANISM: Artificial Sequence
<220> FEATURE:
<223> OTHER INFORMATION: Extension Primer

<400> SEQUENCE: 14
tgctacattt gctttcttc                                              19

<210> SEQ ID NO 15
<211> LENGTH: 21
<212> TYPE: DNA
<213> ORGANISM: Artificial Sequence
<220> FEATURE:
<223> OTHER INFORMATION: Extension Primer

<400> SEQUENCE: 15
ctgagatggc cacaggactc c                                           21

<210> SEQ ID NO 16
<211> LENGTH: 16
<212> TYPE: DNA
<213> ORGANISM: Artificial Sequence
<220> FEATURE:
<223> OTHER INFORMATION: Extension Primer

<400> SEQUENCE: 16
agtcctgtgg ccagcc                                                 16

<210> SEQ ID NO 17
<211> LENGTH: 17
<212> TYPE: DNA
<213> ORGANISM: Artificial Sequence
<220> FEATURE:
<223> OTHER INFORMATION: Extension Primer

<400> SEQUENCE: 17
accaacacct ttccact                                                17

<210> SEQ ID NO 18
<211> LENGTH: 18
<212> TYPE: DNA
<213> ORGANISM: Artificial Sequence
<220> FEATURE:
<223> OTHER INFORMATION: Extension Primer

<400> SEQUENCE: 18
gcatggagct cccgcaag                                               18

<210> SEQ ID NO 19
<211> LENGTH: 16
<212> TYPE: DNA
<213> ORGANISM: Artificial Sequence
<220> FEATURE:
<223> OTHER INFORMATION: Extension Primer

<400> SEQUENCE: 19
acgaaatggc ataggt                                                 16

<210> SEQ ID NO 20
<211> LENGTH: 19
<212> TYPE: DNA
<213> ORGANISM: Artificial Sequence
<220> FEATURE:
<223> OTHER INFORMATION: Extension Primer

<400> SEQUENCE: 20
attgccatac ttctgaaaa                                                    19

<210> SEQ ID NO 21
<211> LENGTH: 20
<212> TYPE: DNA
<213> ORGANISM: Artificial Sequence
<220> FEATURE:
<223> OTHER INFORMATION: Extension Primer

<400> SEQUENCE: 21
gacatattgt tcaacattgc                                                   20

<210> SEQ ID NO 22
<211> LENGTH: 15
<212> TYPE: DNA
<213> ORGANISM: Artificial Sequence
<220> FEATURE:
<223> OTHER INFORMATION: Extension Primer

<400> SEQUENCE: 22
ccgttaacct ctgcg                                                        15

<210> SEQ ID NO 23
<211> LENGTH: 22
<212> TYPE: DNA
<213> ORGANISM: Artificial Sequence
<220> FEATURE:
<223> OTHER INFORMATION: Extension Primer

<400> SEQUENCE: 23
tcgacaggta cttagccagc ac                                                22

<210> SEQ ID NO 24
<211> LENGTH: 21
<212> TYPE: DNA
<213> ORGANISM: Artificial Sequence
<220> FEATURE:
<223> OTHER INFORMATION: Extension Primer

<400> SEQUENCE: 24
gattcctact gtgttttttt t                                                 21

<210> SEQ ID NO 25
<211> LENGTH: 17
<212> TYPE: DNA
<213> ORGANISM: Artificial Sequence
<220> FEATURE:
<223> OTHER INFORMATION: Extension Primer

<400> SEQUENCE: 25
aggaacattc catgtga                                                      17

<210> SEQ ID NO 26
<211> LENGTH: 26
<212> TYPE: DNA
<213> ORGANISM: Artificial Sequence
<220> FEATURE:
<223> OTHER INFORMATION: Extension Primer

<400> SEQUENCE: 26
caaccaattc agaccacatg acattc                                            26

<210> SEQ ID NO 27

-continued

<210> SEQ ID NO 27
<211> LENGTH: 15
<212> TYPE: DNA
<213> ORGANISM: Artificial Sequence
<220> FEATURE:
<223> OTHER INFORMATION: Extension Primer

<400> SEQUENCE: 27
taccccaggc caatc                                                    15

<210> SEQ ID NO 28
<211> LENGTH: 25
<212> TYPE: DNA
<213> ORGANISM: Artificial Sequence
<220> FEATURE:
<223> OTHER INFORMATION: Amplification Primer for Qualitative PCR

<400> SEQUENCE: 28
tgttgaacaa tatgtctttg gtcta                                         25

<210> SEQ ID NO 29
<211> LENGTH: 21
<212> TYPE: DNA
<213> ORGANISM: Artificial Sequence
<220> FEATURE:
<223> OTHER INFORMATION: Amplification Primer for Qualitative PCR

<400> SEQUENCE: 29
gaaggaattt gatcgcgtta c                                             21

<210> SEQ ID NO 30
<211> LENGTH: 19
<212> TYPE: DNA
<213> ORGANISM: Artificial Sequence
<220> FEATURE:
<223> OTHER INFORMATION: Amplification Primer for Qualitative PCR

<400> SEQUENCE: 30
ggtggtggtc ctcaccctg                                                19

<210> SEQ ID NO 31
<211> LENGTH: 21
<212> TYPE: DNA
<213> ORGANISM: Artificial Sequence
<220> FEATURE:
<223> OTHER INFORMATION: Amplification Primer for Qualitative PCR

<400> SEQUENCE: 31
gttcgcaaga ttcgatggtc g                                             21

<210> SEQ ID NO 32
<211> LENGTH: 26
<212> TYPE: DNA
<213> ORGANISM: Artificial Sequence
<220> FEATURE:
<223> OTHER INFORMATION: Amplification Primer for Qualitative PCR

<400> SEQUENCE: 32
ggatattctc agtcatgcat ctgtgt                                        26

<210> SEQ ID NO 33
<211> LENGTH: 18
<212> TYPE: DNA
<213> ORGANISM: Artificial Sequence
<220> FEATURE:
<223> OTHER INFORMATION: Amplification Primer for Qualitative PCR

<400> SEQUENCE: 33

```
ttcgatggtc gggttcca                                                          18

<210> SEQ ID NO 34
<211> LENGTH: 13
<212> TYPE: DNA
<213> ORGANISM: Artificial Sequence
<220> FEATURE:
<223> OTHER INFORMATION: Amplification Primer for Qualitative PCR
<220> FEATURE:
<221> NAME/KEY: modified_base
<222> LOCATION: (1)..(1)
<223> OTHER INFORMATION: 6-carboxyfluorescein
<220> FEATURE:
<221> NAME/KEY: modified_base
<222> LOCATION: (13)..(13)
<223> OTHER INFORMATION: Minor Groove Binder

<400> SEQUENCE: 34
ccccaggcca atc                                                               13
```